US 7,022,327 B1

(12) United States Patent
Lütticken et al.

(10) Patent No.: US 7,022,327 B1
(45) Date of Patent: Apr. 4, 2006

(54) RECOMBINANT BIRNAVIRUS VACCINE

(75) Inventors: Heinrich Dieter Lütticken, Boxmeer (NL); Egbert Mundt, Millienhagen (DE); Adriaan Anthonius Wilhelmus Maria van Loon, Sambeek (NL)

(73) Assignee: Akzo Nobel N.V., Arnhem (NL)

( * ) Notice: Subject to any disclaimer, the term of this patent is extended or adjusted under 35 U.S.C. 154(b) by 78 days.

(21) Appl. No.: 09/084,837

(22) Filed: May 26, 1998

(30) Foreign Application Priority Data

May 26, 1997 (EP) .................................. 97201599

(51) Int. Cl.
  *A61K 39/12* (2006.01)
  *C12N 7/00* (2006.01)
  *C12N 7/01* (2006.01)
  *C12N 7/04* (2006.01)
  *C07H 21/04* (2006.01)

(52) U.S. Cl. ................. 424/204.1; 424/199.1; 435/235.1; 435/236; 536/23.72; 536/24.1

(58) Field of Classification Search ............. 435/235.1, 435/236, 5; 424/204.1, 199.1; 536/23.72, 536/24.1
See application file for complete search history.

(56) References Cited

U.S. PATENT DOCUMENTS 5,279,965 A * 1/1994 Keeler ..................... 435/320.1
5,328,688 A * 7/1994 Roizman ................. 424/205.1
5,690,937 A * 11/1997 Parkin et al. ............ 424/199.1
5,993,824 A * 11/1999 Murphy et al. .......... 424/211.1

FOREIGN PATENT DOCUMENTS

WO           91/02795     * 3/1991
WO     WO 95/26196       10/1995

OTHER PUBLICATIONS

Heppell et al. Journal of General virology 76: 2091-2096, 1995.*
Mundt, E. Bundesforchungsanstalt fur Viruskrankheiten de Tiere; Jahresbericht 1996, p. 51, published Apr. 16, 1997 (with English translation).*
Lewin, B. Genes IV, p. 70-73, Oxford University Press, 1990.*
Culver et al. Virology 173:755-758, 1989.*

(Continued)

*Primary Examiner*—Shanon Foley
(74) *Attorney, Agent, or Firm*—William M. Blackstone; William P. Ramey, III; Mary Gormley

(57) ABSTRACT

The present invention provides a birnavirus mutant which is suited as vaccine candidate in eradication control programmes. The mutant is not able to produce a native VP5 protein, and this feature can be used as a marker to distinguish between animals vaccinated with the VP5 mutant or infected with a naturally-occurring birnavirus.

8 Claims, 5 Drawing Sheets

OTHER PUBLICATIONS

Figure 2:
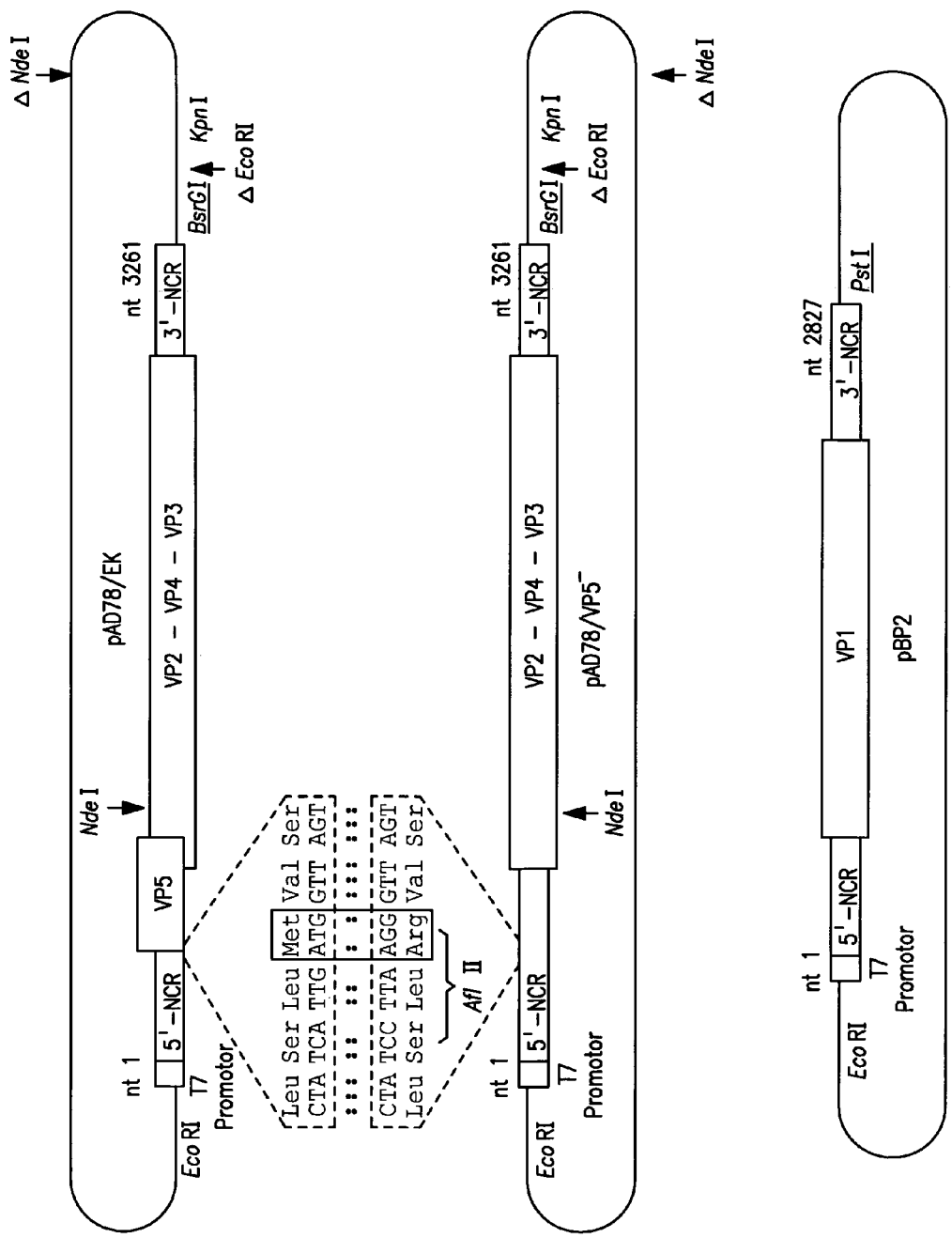

Kibenge et al. 1988. Growth of serotypes I and II and variant strains of infectious bursal disease virus in Vero cells. Avian Diseases vol. 32 (2): p. 298-303, (abstract only cited).*

Murphy et al. Journal of Leukocyte Biology. 1994; 56 (3): 294-303, abstract only.*

Fernholz et al. Virology. 1993; 197 (1): 64-73, abstract only.*

E. Mundt et al., *Proc. Natl. Acad. Sci. USA*, 93:11131-11136, 1996.

E. Mundt et al., *Journal of General Virology*, 76:437-443, 1995.

E. Mundt et al., *Journal of Virology*, 71:7:5647-5651, 1997.

Yao et al., "Generation of a Mutant Infectious Bursal Disease Virus That Does Not Cause Bursal Lesions", *Journal of Virology*, Apr. 1998 p. 2647-2654.

* cited by examiner

Genomic organization of segment A of strain D78 and segment B of strain P2

D78 segment A nt 1 — 5'-NCR — nt 97 — AUG — VP5 — nt 531 — UGA — AUG — nt 131 — VP2 – VP4 – VP3 — nt 3166 — UGA — 3'-NCR — nt 3261

P2 segment B nt 1 — 5'-NCR — nt 112 — AUG — VP1 — nt 2745 — UAA — 3'-NCR — nt 2827

FIG. 1

FIG. 5

RECOMBINANT BIRNAVIRUS VACCINE

FIELD OF THE INVENTION

The present invention is concerned with a birnavirus mutant, a vaccine comprising this mutant, a method for determining birnavirus infection in an animal, as well as with a test kit for carrying out this method.

BACKGROUND OF THE INVENTION

Infectious bursal disease virus (IBDV) and Infectious pancreatic necrosis virus (IPNV) are members of the Birnaviridae family. Viruses in this family have a very similar genomic organisation and a similar replication cycle. The genomes of these viruses consist of 2 segments (A and B) of double-stranded (ds) RNA. The larger segment A encodes a polyprotein which is cleaved by autoproteolysis to form mature viral proteins VP2, VP3 and VP4 (Hudson, P. J. et al, Nucleic Acids Res., 14, 5001–50012, 1986; Dobos P., Annual review of fish diseases 5, 25–54, 1995). VP2 and VP3 are the major structural proteins of the virion. VP2 is the major host-protective immunogen of birnaviruses, and contains the antigenic regions responsible for the induction of neutralising antibodies. The VP4 protein appears to be a virus-coded protease that is involved in the processing of a precursor polyprotein of the VP2, VP3 and VP4 proteins. The larger segment A possesses also a second open reading frame (ORF), preceding and partially overlapping the polyprotein gene. This second open reading frame encodes a protein VP5 of unknown function that is present in IBDV infected cells (Mundt, E. et al., J. Gen. Virol., 76, 437–443, 1995).

The smaller segment B encodes VP1, a 90 kDa multifunctional protein with polymerase and capping enzyme activities (Spies, U. et al., Virus Res., 8, 127–140, 1987 and Spies, U. et al., J. Gen. Virol., 71, 977–981, 1990; Duncan R. et al., Virology 181, 541–552, 1991).

For IBDV, two serotypes exist, serotype 1 and 2. The 2 serotypes may be differentiated by virus neutralisation (VN) tests. Furthermore, subtypes of serotype 1 have been isolated. These so-called "variant" viruses of serotype 1 can be identified by cross-neutralisation tests (Diseases of Poultry, 9th edition, 1991, Wolfe Publishing Ltd, ISBN 0 7234 1706 7, Chapter 28, P. D. Lukert and Y. M. Sailf, 648–663), a panel of monoclonal antibodies (Snyder, D. B. et al., Arch. Virol., 127, 89–101. 1992.) or RT-PCR (Jackwood, D. J., Proceedings of the International symposium on infectious bursal disease and chicken infectious anaemia, Rauischholzhausen, Germany, 155–161, 1994). Some of these subtypes of serotype 1 of IBDV have been described in literature for example: Classical, Variant-E, GLS, RS593 and DS326 strains (Van Loon, et al. Proceedings of the International symposium on infectious bursal disease and chicken infectious anaemia, Rauischholzhausen, Germany, 179–187, 1994).

Infectious Bursal disease (IBD), also called Gumboro disease, is an acute, highly-contagious viral infection in chickens that has lymphoid tissue as its primary target with a selective tropism for cells of the bursa of Fabricius. The morbidity rate in susceptible flocks is high, with rapid weight loss and moderate mortality rates. Chicks that recover from the disease may have immune deficiencies because of the destruction of the bursa of Fabricius which is essential to the defence mechanism of the chicken. The IBD-virus causes severe immunosuppression in chickens younger than 3 weeks of age and induces bursal lesions in chicks up to 3 months old.

For many years the disease could be prevented by inducing high levels of antibodies in breeder flocks by the application of an inactivated vaccine, to chickens that had been primed with attenuated live IBDV vaccine. This has kept economic losses caused by IBD to a minimum. Maternal antibodies in chickens derived from vaccinated breeders prevents early infection with IBDV and diminishes problems associated with immunosuppression. In addition, attenuated live vaccines have also been used successfully in commercial chicken flocks after maternal antibodies had declined.

Recently, very virulent strains of IBDV have caused outbreaks of disease with high mortality in Europe. The current vaccination programs failed to protect chicks sufficiently. Vaccination failures were mainly due to the inability of live vaccines to infect the birds before challenge with virulent field virus.

Eradication of the disease by other preventative measures than vaccination has not been feasible, because the virus is widely spread and because with currently administered live attenuated or inactivated IBDV vaccines it is not possible to determine whether a specific animal is infected with an IBDV field virus or whether the animal was vaccinated with an IBDV vaccine. In order to be able to start an eradication control programme for IBDV it is highly desirable that the possibility exists to discriminate between animals vaccinated with an IBDV vaccine and those infected with a field virus so as to be able to take appropriate measures, i.e. remove infected flocks, to reduce spreading of the virulent field virus. The introduction of, for example, a serologically identifiable marker can be achieved by introducing a mutation in genes encoding non-essential (glyco)proteins of the IBDV which still give rise to the production of antibodies in an infected host animal. A marker vaccine for Aujeszky's disease and companion diagnostic tests have proven their practical value in the control of this disease. Whereas such control programs for other viral infectious diseases in animals are under development, until the present invention a vaccine based on an IBDV vaccine strain which would fit in IBDV control programs has not been described yet. The main reason for this is that the prerequisites for the development for such an IBDV marker vaccine were not met. No permissive position or region in the genomic IBDV sequence, i.e. a position or region which can be used for the incorporation of the mutation without disrupting essential functions of IBDV, such as those necessary for infection and replication, have been identified yet. Moreover, such a non-essential region in the IBDV genome should encode a (glyco)protein which elicits a major serological response in an animal infected with wild-type IBDV, and such a region was not identified before.

SUMMARY OF THE INVENTION

The present inventors have unexpectedly found a non-essential gene within segment A of a birnavirus genome which can be mutated such that the resulting birnavirus mutant does not produce the native expression product of that gene. Moreover, it has been found that this birnavirus mutant can be used as a marker vaccine virus which allows to make a serological distinction between animals infected with wild-type birnavirus and animals immunised with a vaccine based on this birnavirus mutant.

DETAILED DESCRIPTION OF THE INVENTION

The present invention provides a birnavirus mutant which is not able to produce a native VP5 protein as a result of a mutation in the VP5 gene of the birnavirus genome.

Preferably, the birnavirus mutant is an IBDV mutant or an IPNV mutant, the IBDV mutant being most preferred, in particular an IBDV mutant derived from a serotype I IBD virus is provided by the present invention.

The inventors have found that an IBDV mutant which is not able to produce the native VP5 protein is still able to infect cells and to replicate in these cells in vitro. It is demonstrated that the IBDV mutant according to the invention is replication competent in cell culture (Example 2). The VP5⁻ IBDV exhibits a delay in replication in chicken embryo cells as compared to the VP5⁺ parental virus, however, final yields of the virus are similar, i.e. about $10^{7.5}$ $TCID_{50}$/ml (Example 1). Moreover, it is demonstrated that the IBDV mutant is also able to infect poultry and to replicate in the infected host animals in vivo, i.e. evidence is provided that the gene encoding the VP5 protein is a non-essential gene. Example 3 shows that the VP5⁻ IBDV can be re-isolated from organs of animals infected with the IBDV mutant and that the IBDV mutant induces a protective immune response in the infected animals.

Moreover, it has been established herein that part of the normal anti-IBDV immune response in poultry is directed to the VP5 region. This is rather surprising as the VP5 protein is considered to represent a non-structural viral protein (Mundt et al., J. Gen. Virol. 76, 437–443, 1995) and the immune response in an animal against a viral pathogen is usually elicited against the structural (glyco)proteins of the virus. These findings make the IBDV mutant and other birnavirus mutants according to the present invention a suitable vaccine candidate for a marker vaccine. Such a marker vaccine provides the possibility to determine whether animals are infected with a wild-type birnavirus, e.g. IBDV, or with a vaccine virus.

Additionally, it has been found that the VP5 protein is involved in the expression of virulence of the birnaviruses, in particular of IBDV, and that the inability of the virus mutants to produce the native VP5 protein leads to an attenuation of the virus.

With the term "which is not able to produce a native VP5 protein" is meant that the birnavirus mutant produces a polypeptide that can be distinguished by serological tests from the native VP5 protein, or does not produce a VP5 protein at all. For example, in the former case, the birnavirus mutant produces only a fragment of the native birnavirus VP5 protein which lacks one or more immunogenic epitopes.

Preferably, the birnavirus mutant according to the invention produces no VP5 protein upon infection of a host cell.

Figure 3:
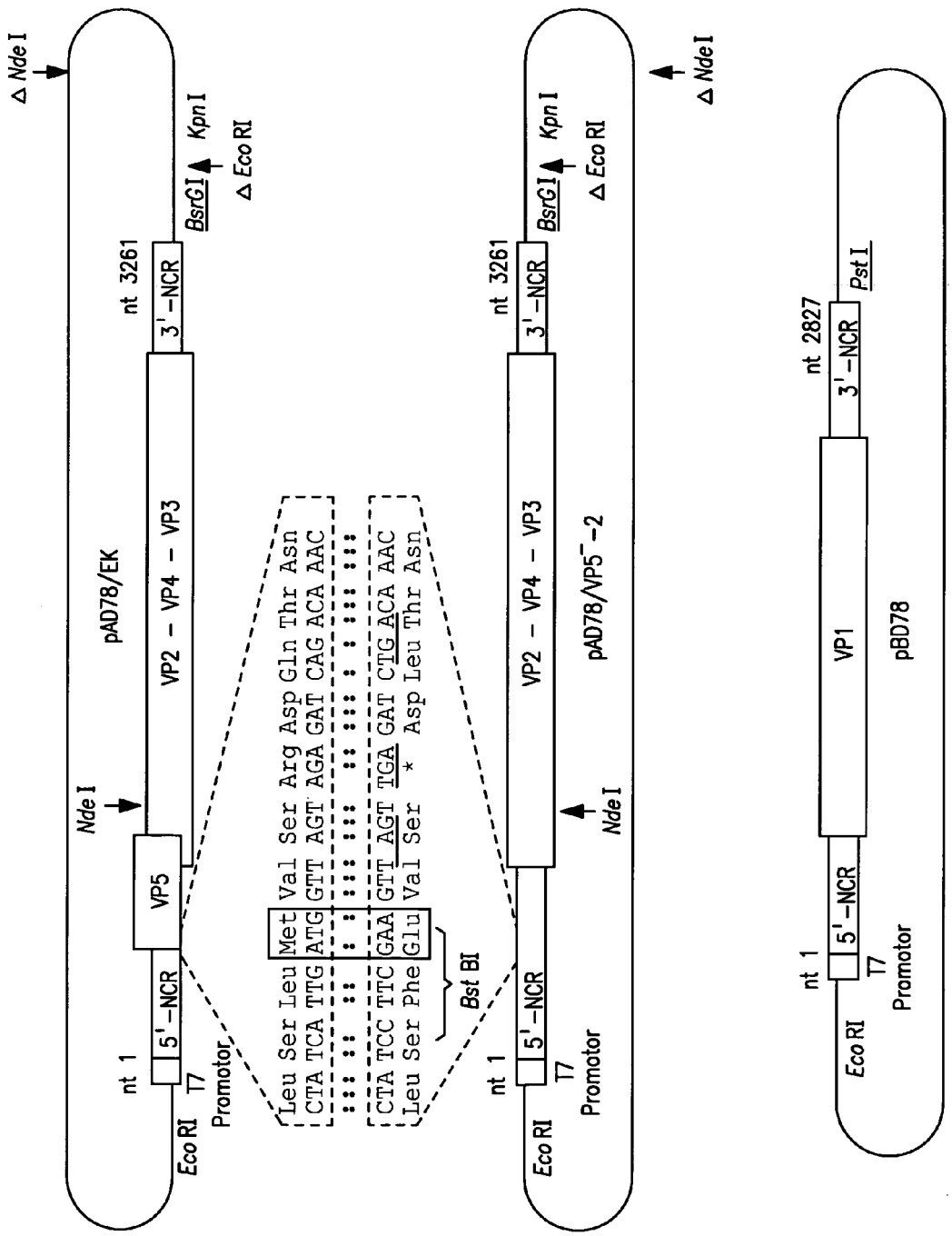

As described above, the genomic organisation of the birnaviruses is well established: the IBDV and IPNV genome comprises a large segment A and a smaller segment B. The segment A of IBDV comprises a large open reading frame (ORF) encoding a polyprotein of about 110 kDa (VP2-VP4-VP3). The gene encoding the VP5 protein is identified in the prior art, and defined herein, as the small ORF on segment A of the birnavirus genome which precedes and partially overlaps the polyprotein encoding ORF (Bayliss et al., J. Gen. Virol. 71, 1303–1312, 1990; Spies et al., J. Gen. Virol. 71, 977–981, 1990; Havarstein L. S. et al., J. Gen. Virology 71, 299–308; 1990; Dobos et al., 1995, supra; FIGS. 1–3 herein and SEQ ID No.'s 1–7). The mutation introduced in the VP5 gene is such that it does not prevent the expression of the polyprotein.

SEQ ID No. 1 comprises the full length cDNA nucleotide sequence of segment B of IBDV strain P2, as well as the amino acid sequence of the VP1 protein encoded by segment B (see also SEQ ID. No. 2). SEQ ID No. 3 and 5 depict the full length cDNA sequence of segment A of IBDV strain D78 and the coding region of the VP5 protein and the polyprotein, respectively. SEQ ID 3 and 4 also show the amino acid sequence of the D78 VP5 protein. SEQ ID No. 5 and 6 show the amino acid sequence of the polyprotein VP2-VP4-VP3 of D78. SEQ ID No. 7 shows the 5'-end of segment A of strain D78, including the mutations introduced in the VP5 coding region. SEQ ID No. 8 shows the nucleotide sequence of segment B of strain D78 and the amino acid sequence of the D78 VP1 protein. The genomic organisation of both segments is also shown in FIG. 1.

The ORF coding for VP5 is conserved in all hitherto published segment A sequences. The IBDV ORF encodes 145 amino acids resulting in a calculated molecular mass of 16.5 kDa. The nucleotide sequence of the ORF encoding the VP5 protein of IBDV strain D78 used herein is shown in SEQ ID No. 3 and 4. Natural variations may exist between individual IBDV isolates. These natural variations result from small differences in the genomes of these viruses. The nucleotide sequence of the segment A, including the nucleotide sequence of the VP5 gene for many IBDV isolates have been described in the prior art (Vakharia et al., Avian Diseases 36, 736–742, 1992; Bayliss et al., J. Gen. Virol. 71, 1303–1314, 1990; Hudson et al., Nuc. Acid Res. 14, 5001–5012, 1986; Schnitzler et al., J. Gen. Virol. 47, 1563–1571, 1993; Kibenge et al., J. Gen. Virol. 71, 569–577, 1990 and Virology 184, 437–440, 1991; Mundt et al., Virology 209, 10–18, 1995; Lana et al., Virus Genes 6, 247–259, 1992; Vakharia et al., Virus Res. 31, 265–273, 1994; Brown et al., Virus Res. 40, 1–15, 1996). The amino acid sequence of the VP5 protein from serotype I IBDV strains display a homology of at least 95% with the VP5 amino acid sequence shown in SEQ ID No. 3 and 4, whereas the homology between serotype II VP5 sequence and the amino acid sequence shown in SEQ ID No. 3 and 4 is at least 75%. Therefore, a preferred IBDV mutant according to the present invention is an IBDV mutant wherein the mutation is introduced in the VP5 gene having a homology of at least 75%, in particular at least 95% on the amino acid sequence level with the VP5 amino acid sequence shown herein.

Preferably an IBDV mutant according to the present invention is derived from any of the classical or variant (e.g. variant E or GLS) IBDV vaccine strains, such as those currently used in the field. Such suitable IBDV strains include the IBDV vaccine strains present in the commercially available vaccines: D78, PBG 98, LZ 228E, 89-03 (Intervet International B.V.), Bursine 2 (Fort Dodge Animal Health) and S 706 (Rhône Mérieux).

A particular preferred IBDV mutant according to the invention is derived from the D78 strain comprising a VP5 gene encoding a protein having the amino acid sequence shown in SEQ ID No. 3 and 4.

Alternatively, the parent birnavirus strain for the virus mutant according to the invention is a virulent birnavirus field strain. It is found herein that the VP5 protein is a factor associated with virulence, and that the absence of the native VP5 protein in a birnavirus results in an attenuated form of the virus.

Preferably the invention provides a birnavirus mutant which is not able to produce a native VP5 protein as a result of a mutation in the part of the VP5 gene which does not overlap with the large ORF encoding the polyprotein.

In particular, the birnavirus mutant according to the invention comprises a mutation in the 5'-end of the VP5 gene spanning nucleotides 1–30, preferably 1–20, more preferably 1–10. Most preferred is an birnavirus mutant having a mutation in nucleotides 1–3 of the VP5 gene.

A mutation is understood to be a change of the genetic information in the VP5 gene with respect to the genetic information present in this region of the genome of naturally occurring birnavirus producing native VP5 protein. The mutation is, for example, a nucleic acid substitution, deletion, insertion or inversion, or a combination thereof.

In a preferred embodiment of the present invention a birnavirus mutant is provided wherein the mutation is a substitution of one or more nucleotides. In particular, a nucleic acid substitution is introduced in the start codon, as a result of which the new codon encodes an amino acid different from methionine or represents a stop codon, preferably the nucleic acid substitution comprises at least two of the nucleotides of the start codon.

A further birnavirus mutant according to the invention comprises a substitution of one or more nucleotides in a codon(s) different from the start codon resulting in one or more stop codons, preferably in the 5'-end of the VP5 gene as defined above, if desired in addition to a substitution in the start codon as described above. Preferably, the birnavirus mutant comprises a stop codon in this region of the VP5 gene in each of the three reading frames.

Such a preferred birnavirus mutant may be an IBDV mutant having a mutation in the start codon, the fourth and the sixth codon of the VP5 gene, preferably resulting in the mutated codons shown in SEQ ID No. 7 and FIG. 3.

Alternatively, a birnavirus mutant is provided wherein the mutation is a deletion. In particular, the deletion comprises less than 20, less than 10 or less than 5 nucleotides. Preferably, the deletion comprises a total number of nucleotides not dividable by three, resulting in a shift of the reading frame.

Preferably the deletion comprises one or more nucleotides of the start codon of the VP5 gene.

In an alternative embodiment of the present invention a birnavirus mutant is provided wherein the mutation comprises the insertion of a heterologous nucleic acid sequence in the birnavirus genome. A heterologous nucleic acid sequence is a nucleic acid sequence normally not present at the specific insertion site of the particular virus species.

The heterologous nucleic sequence to be incorporated into the birnavirus genome is a nucleic acid fragment which either encodes a polypeptide or is a non-coding sequence. The nucleic acid fragment can be derived from any source, e.g. viral, eukaryotic, prokaryotic or synthetic, including oligonucleotides suitable for the interruption of the expression of the VP5 gene.

A suitable oligonucleotide for the interruption of the VP5 expression may comprise three translational stop codons in each of the possible reading frames in both directions, in addition to one or more appropriate restriction enzyme cleavage sites useful for the insertion of a second heterologous nucleic acid sequence. The length and nucleotide sequence of such a non-coding heterologous nucleic acid sequence is not critical, but preferably varies between 8–50 nucleotides.

In a further embodiment of the present invention a birnavirus mutant is provided which can be used not only for the preparation of a vaccine against infection by a specific birnavirus, but also against other poultry or fish infectious diseases. For example, a vector vaccine based on such an IBDV mutant offers the possibility to immunise against other avian pathogens by the expression of antigens of these avian pathogens within infected cells of the immunised host. Such an IBDV vector according to the present invention can be obtained by inserting a heterologous nucleic acid sequence encoding a polypeptide heterologous to the IBDV in the VP5 gene as defined herein.

The heterologous nucleic acid sequence may encode an antigen of an avian pathogen such as Newcastle disease virus, Infectious bronchitis virus, Marek's disease virus, avian encephalomyelitis virus, avian reovirus, avian influenza virus, chicken anaemia virus, *Salmonella* spp., *E. coli*, and *Eimeria* spp.

Furthermore, an IBDV mutant according to the invention comprises in addition to the mutation in the VP5 gene, a mutation in the VP2 gene, wherein this gene expresses a chimeric protein comprising neutralising epitopes of more than one antigenic type of IBDV (e.g. classic, Variant-E and/or GLS). Preferably, such a mutant comprises the relevant protective VP2 epitopes of a variant GLS strain and classic strain. In particular, the mutated VP2 gene is a GLS VP2 gene comprising a nucleic acid sequence fragment encoding the B69 epitope. The construction of such a mutated VP2 genes is described in Snyder et al., Avian Diseases 38, 701–707, 1994.

Furthermore, nucleic acid sequences encoding polypeptides for pharmaceutical or diagnostic applications, in particular immuno-modulators such as lymphokines, interferons or cytokines, may be incorporated into the VP5 gene. The heterologous nucleic acid sequence may also encode a screenable marker, such as *E. coli* β-galactosidase or *E. coli* β-glucuronidase.

The construction of birnavirus mutants, in particular of IBDV mutants according to the present invention can be achieved by means of the recently established infectious cRNA system for IBDV (Mundt and Vakharia, Proc. Natl. Acad. Sci. USA 93, 11131–11136, 1996). This reverse genetics system opens the possibility to introduce mutations in the RNA genome of the IBD virus, in particular in the VP5 gene. The most important step in this reverse genetics system is to provide full length cDNA clones of the segments A and B of IBD virus. cDNA constructs comprising the segment A or B, including the nucleotides of the 5'- and 3'-ends of both these segments can be generated according to the method described by Mundt and Vakharia (1996, supra). Additionally, these constructs comprise a RNA polymerase promoter operably linked to either of the segments. The promoter can be the promoter for the T7, SP6 or T3 polymerase, the T7 promoter being preferred. Mutations can be introduced into the VP5 gene by means of methods generally known in the art for this purpose. In particular, the mutation(s) are introduced by means of site directed mutagenesis.

For example, in a first step a cDNA fragment is provided comprising at least a substantial part of the VP5 gene. In the next step suitable primer pairs are designed and hybridised with the VP5 sequence containing fragment. The 5'-primer comprises in addition to sequences complementary to the VP5 sequence, nucleotides which harbour the desired mutation, e.g. a mutation which changes the ATG start codon to an AGG (arginine) codon. Moreover, the 5'-primer is provided with an upstream nucleotide sequence representing a suitable restriction enzyme cleavage site which allows the restoring of the complete 5'-end non-coding sequence. Subsequently, the new mutated fragment is amplified using PCR and the new fragment is introduced in the starting sequence by replacing the native nucleic acid sequence using appropriate restriction enzymes. In the next step plus-sense transcripts of the segment A and B are generated in vitro with (T7) RNA polymerease, after which the synthetic transcripts are purified using conventional RNA purification techniques. The recombinant IBDV mutant according to the invention is obtained after transfection of suitable cells (e.g. VERO cells, QM-7 cells or CEC cells) with the synthetic RNA transcripts of both segments of the IBDV genome, if desired in the presence of transfection-enhancing compositions, such as Lipofectin. Finally the recombinant IBDV is harvested from the supernatant of the transformed cells.

Methods for introducing a mutation in the birnavirus genome are described herein, but are also generally used in the art (Mundt and Vakharia, 1996, supra; Current Protocols in Molecular Biology, eds.: F. M. Ausubel et al., Wiley N.Y., 1995 edition, pages 8.5.1.–8.5.9.)

Further to the unexpected finding by the present inventors that the VP5 ORF of IBDV is a non-essential region of the IBDV genome, it has also been found that an IBDV mutant according to the present invention is able to induce a protective immune response, i.e. animals immunised with a vaccine comprising the IBDV mutant are protected against virulent challenge. Moreover, it has been found that anti-sera of animals infected with naturally occurring IBDV comprise antibodies directed to the non-structural VP5 protein and that these antisera can be distinguished from anti-sera derived from animals infected with an IBDV mutant according to the present invention. In addition, it has been found that the IBDV mutant as described above is attenuated if compared with the parent IBD virus which is able to produce the native VP5 protein.

Therefore, another aspect of this invention is a vaccine for use in the protection of animals against birnavirus infection comprising the birnavirus mutant as characterised above, together with a pharmaceutical acceptable carrier or diluent. In particular, the vaccine according to the invention is a vaccine for use in the protection of poultry against infectious bursal disease comprising the IBDV mutant described above.

The birnavirus mutant according to the present invention can be incorporated into the vaccine as live or inactivated virus.

A vaccine according to the invention can be prepared by conventional methods such as for example commonly used for the commercially available live- and inactivated IBDV vaccines. Briefly, a susceptible substrate is inoculated with an IBDV mutant according to the invention and propagated until the virus replicated to a desired infectious titre after which IBDV containing material is harvested.

Every substrate which is able to support the replication of IBD viruses can be used in the present invention, including primary (avian) cell cultures, such as chicken embryo fibroblast cells (CEF) or chicken kidney cells (CK), mammalian cell lines such as the VERO cell line or the BGM-70 cell line, or avian cell lines such as QT-35, QM-7 or LMH. Usually, after inoculation of the cells, the virus is propagated for 3–10 days, after which the cell culture supernatant is harvested, and if desired filtered or centrifuged in order to remove cell debris.

Alternatively, the IBDV mutant is propagated in embryonated chicken eggs. In particular, the substrate on which these IBD viruses are propagated are SPF embryonated eggs. Embryonated eggs can be inoculated with, for example 0.2 ml IBDV mutant containing suspension or homogenate comprising at least $10^2$ TCID$_{50}$ per egg, and subsequently incubated at 37° C. After about 2–5 days the IBD virus product can be harvested by collecting the embryo's and/or the membranes and/or the allantoic fluid followed by appropriate homogenising of this material. The homogenate can be centrifuged thereafter for 10 min at 2500×g followed by filtering the supernatant through a filter (100 µm).

The vaccine according to the invention containing the live virus can be prepared and marketed in the form of a suspension or in a lyophilised form and additionally contains a pharmaceutically acceptable carrier or diluent customary used for such compositions. Carriers include stabilisers, preservatives and buffers. Suitable stabilisers are, for example SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are the same as mentioned below.

Although administration by injection, e.g. intramuscular, subcutaneous of the live vaccine according to the present invention is possible, the vaccine is preferably administered by the inexpensive mass application techniques commonly used for IBDV vaccination. For IBDV vaccination these techniques include drinking water and spray vaccination.

Alternative methods for the administration of the live vaccine include in ovo, eye drop and beak dipping administration.

In another aspect of the present invention a vaccine is provided comprising the birnavirus mutant in an inactivated form. The major advantage of an inactivated vaccine is the extremely high levels of protective antibodies of long duration that can be achieved.

The aim of inactivation of the viruses harvested after the propagation step is to eliminate reproduction of the viruses. In general, this can be achieved by chemical or physical means. Chemical inactivation can be effected by treating the viruses with, for example, enzymes, formaldehyde, β-propiolactone, ethylene-imine or a derivative thereof. If necessary, the inactivating compound is neutralised afterwards. Material inactivated with formaldehyde can, for example, be neutralised with thiosulphate. Physical inactivation can preferably be carried out by subjecting the viruses to energy-rich radiation, such as UV light or γ-rays. If desired, after treatment the pH can be adjusted to a value of about 7.

A vaccine containing the inactivated birnavirus mutant can, for example comprise one or more of the above-mentioned pharmaceutically acceptable carriers or diluents suited for this purpose.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F® or Marcol 52® or a vegetable oil such as vitamin E acetate, and saponins.

The vaccine according to the invention comprises an effective dosage of the birnavirus mutant as the active component, i.e. an amount of immunising birnavirus material that will induce immunity in the vaccinated birds against challenge by a virulent virus. Immunity is defined herein as the induction of a significant higher level of protection in a population of birds after vaccination compared to an unvaccinated group.

Typically, the live vaccine according to the invention can be administered in a dose of $10^2$–$10^9$ TCID$_{50}$ infectious dose$_{50}$ (TCID$_{50}$) per animal, preferably in a dose ranging from $10^{5.0}$–$10^{7.0}$ TCID$_{50}$, and an inactivated vaccines may contain the antigenic equivalent of $10^5$–$10^9$ TCID$_{50}$ per animal.

Inactivated vaccines are usually administered parenterally, e.g. intramuscularly or subcutaneously.

Although, the IBDV vaccine according to the present invention may be used effectively in chickens, also other poultry such as turkeys, guinea fowl and partridges may be successfully vaccinated with the vaccine. Chickens include broilers, reproduction stock and laying stock.

The age of the animals receiving a live or inactivated vaccine according to the invention is the same as that of the animals receiving the conventional live- or inactivated IBDV vaccines. For example, broilers (free of maternally derived antibodies-MDA) may be vaccinated at one-day-old, whereas broilers with high levels of MDA are preferably vaccinated at 2–3 weeks of age. Laying stock or reproduction stock with low levels of MDA may be vaccinated at 1–10 days of age followed by booster vaccinations with inactivated vaccine on 6–8 and 16–20 weeks of age.

The invention also includes combination vaccines comprising, in addition to the IBDV or IPNV mutant according to the invention, one or more immunogens derived from other pathogens infectious to poultry or fish, respectively.

Preferably, the combination vaccine additionally comprises one or more vaccine strains of infectious bronchitis virus (IBV), Newcastle disease virus (NDV), egg drop syndrome (EDS) virus, turkey rhinotracheitis virus (TRTV) or reovirus.

In addition to a marker vaccine for birnaviruses, the availability of an appropriate diagnostic test is an essential requirement for the application of a birnavirus eradication control programme. Such a diagnostic test is provided herein and comprises a method for determining IBDV infection in poultry and IPNV infection in fish, i.e. it provides a method for distinguishing an animal in the field vaccinated with a vaccine as described above, from an animal infected with a naturally-occurring IBDV or IPNV.

Therefore, the present invention provides a method for the detection of birnavirus infection, in particular for the detection of IBDV infection in an animal comprising the step of examining a sample of the animal for the presence of VP5 antibodies or antigens. The animal is an animal from the field and is in particular an avian species, preferably a chicken. The sample coming from the animal may be any sample in which IBDV antibodies or antigens are present, e.g. a blood, serum or tissue sample, the serum sample being preferred.

A preferred method for determining birnavirus infection in an animal is a method for the detection of antibodies against the VP5 protein, comprising the steps of:

(i) incubating a sample suspected of containing anti-birnavirus antibodies, with VP5 antigen, (ii) allowing the formation of antibody-antigen complex, and (ii) detecting the presence of the antibody-antigen complex.

The design of this immunoassay may vary. For example, the immunoassay may be based upon competition or direct reaction. Furthermore, protocols may use solid supports or may use cellular material. The detection of the antibody-antigen complex may involve the use of labelled antibodies; the labels may be, for example, enzymes, fluorescent-, chemiluminescent-, radio-active- or dye molecules.

Suitable methods for the detection of the VP5 antibodies in the sample include the enzyme-linked immunosorbent assay (ELISA), immunofluorescent test (IFT) and Western blot analysis.

In an exemplifying ELISA, the wells of a polystyrene micro-titration plate are coated with VP5 antigen. Next, the wells of the coated plates are filled with chicken serum and serial dilutions are made. After incubation, chicken anti-VP5 protein serum antibodies are determined by detecting antibody (monoclonal or polyclonal) with the same specificity as the coated one, but which is labelled (e.g. with biotin). The labelled antibody will occupy the free antigens that have not been occupied by anti-VP5 antibodies in the chicken serum. For example, horse radish peroxidase coupled to avidin may be added and the amount of peroxidase is measured by an enzymatic reaction. If no antibodies against VP5 are present in the chicken serum sample then a maximum absorption is obtained. If the serum contains many antibodies against VP5 then a low absorption is expected. Alternatively, after the incubation with chicken serum, the amount of antibodies present in the serum that bound to the VP5 antigen may be determined directly by using an anti-chicken conjugate followed by the enzymatic reaction.

In a sandwich ELISA the wells of a polystyrene micro-titration plate can be coated with a monoclonal antibody directed against the VP5 protein. Next, the wells of these coated plates are incubated with VP5 antigen. After the antigen is captured, the wells are filled with the chicken serum and serial dilutions are made. Subsequently, the protocol as described above may be followed. This test can also be carried out by using polyclonal serum against VP5 instead of the coated monoclonal antibodies.

In another diagnostic test (Western blot analysis), the VP5 antigen (containing) material is subjected to SDS-PAGE. Next, the separated proteins are electroblotted onto nitrocellulose membrane. Thereafter, the membranes can be cut into lanes and the lanes are incubated with the chicken serum. The presence of VP5 antibodies in the sample can be determined by examination whether antibodies bound to the VP5 antigen, for example by using an anti-chicken conjugate followed by an enzymatic reaction. If antibodies against VP5 are present then a band at about 17 kDa is identifiable.

The VP5 antigen may be any VP5 protein (fragment) comprising material which allows the formation of the VP5 antigen-VP5 antibody complex. Preferably, the VP5 antigen comprises the expression product of a conventional recombinant host cell or virus, e.g. such as *E. coli* expressed VP5 (Mundt et al., J. Gen. Virol. 76, 437–443, 1995) or baculovirus expressed protein (Vakharia et al., Vaccine 12, 452–456, 1994; Vakharia et al., J. Gen Virol. 74, 1201–1206, 1993). In a further embodiment of the present invention a diagnostic test kit is provided which is suitable for performing the diagnostic test according to the invention as described above.

In particular, a diagnostic test kit is provided which comprises in addition to the components usually present, the VP5 antigen (if desired coated onto a solid phase) as the immunological reagent. Other components usually present in such a test kit include, biotin or horseradish peroxidase conjugated antibodies, enzyme substrate, washing buffer etc.

To determine birnavirus VP5 antigen in a test sample from an animal in the field, VP5-specific antibodies are used as the immunological reagent, preferably fixed to a solid phase.

The test sample is added, and after an incubation time allowing formation of the antibody-antigen complex, a second labelled antibody may be added to detect the complex.

EXAMPLES

Example 1

Construction and Analysis of Recombinant VP5⁻ IBD Virus

Construction of Full Length VP5⁻ Clone of IBDV Segment A.

To construct a VP5-negative IBDV, the EcoRI site immediately following the 3'-end of the full length cDNA of strain D78 segment A (pUC19FLAD78; Mundt and Vakharia, Proc. Natl. Acad. Sci. USA 93, 11131–11136, 1996) was deleted. An EcoRI-KpnI fragment containing the T7 polymerase binding site followed by the complete segment A sequence was excised and inserted into EcoRI-KpnI cleaved vector pUC18 after inactivation of the unique NdeI within the vector sequence resulting in plasmid pAD78/EK. Thereafter, the genomic region encompassing the initiation codon for VP5 was amplified in two pieces using primers A1F5' and VP5MutR, and VP5MutF and A2R, respectively (see Table 1 for sequence and location of primers). PCR fragments were cloned separately and were subsequently fused via a unique AflII site which had been created by mutations within respective primers (see FIG. 2). An EcoRI-NdeI fragment containing the T7 polymerase binding site, and the 5'-part of segment A including the introduced mutations was excised and used to substitute the wild-type EcoRI-NdeI fragment in pAD78/EK to yield plasmid pAD78/VP5⁻. Of the three mutations introduced one altered the initiation methionine codon for VP5 into an arginine codon (FIG. 2).

filtrated through 0.45 µm filters and stored at −20° C. For the transfection experiments full length cDNA clones of segment A of strain D78 capable of expressing (pAD78/EK) or unable to express VP5 (pAD78/VP5⁻) were transcribed into synthetic RNA and cotransfected with segment B full length cRNA into CEC. Resulting virus progeny IBDV/EK and IBDV/VP5⁻ was further characterised.

Analysis of transfection progeny by immunofluorescence and Radioimmunoprecipitation assay (RIPA). VP5 was expressed in E. coli as described in Mundt et al. (J. Gen. Virol. 76, 437–443, 1995). Rabbit monospecific polyclonal anti serum and mouse monoclonal antibodies against VP5 were prepared according to standard protocols. Vero cells infected with IBDV/VP5⁻, IBDV/EK, and non-infected cells, respectively, were incubated with rabbit anti-IBDV serum, rabbit anti-VP5 serum and with anti-VP5 mAb DIE 7, and stained with fluoresceine-conjugated secondary antibodies. Both antisera and the monoclonal antibody recognised IBDV antigens in the cytoplasm of IBDV/EK infected cells. In contrast, whereas the anti-IBDV serum readily detected viral antigens in IBDV/VP5⁻ infected cells, neither the monospecific anti VP5-serum nor the monoclonal anti-VP5 antibody exhibited specific reactivity. None of these immunological reagents reacted with non-infected controls.

Figure 4:
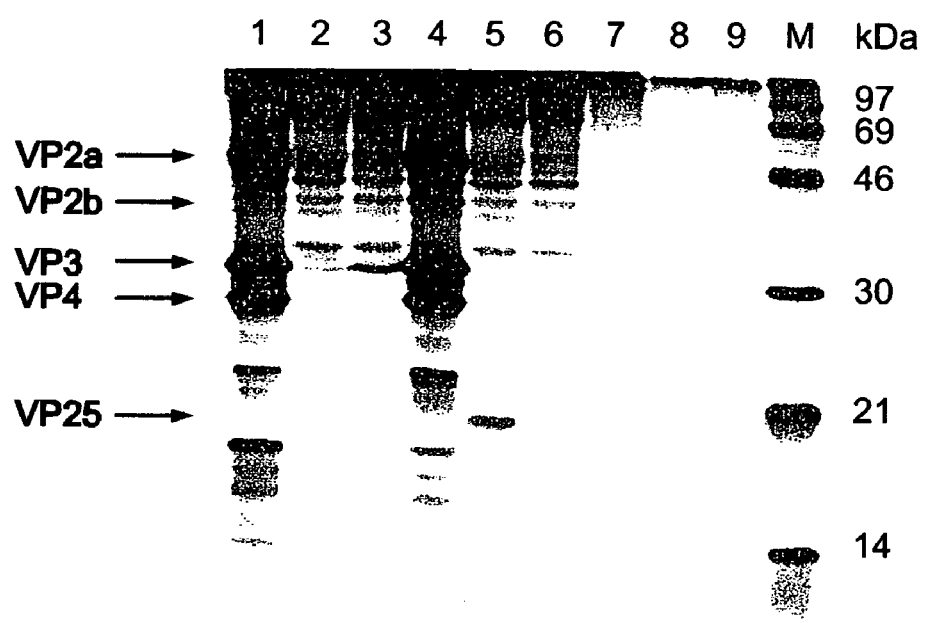

To analyse viral proteins expressed during replication lysates of radioactively labelled CEC infected with IBDV/VP5⁻ (FIG. 4, lanes 1–3) and IBDV/EK (FIG. 4, lanes 4–6) were immunoprecipitated with rabbit anti-IBDV serum, rabbit anti-VP5 serum and mAb DIE 7. Non-infected CEC were used as control (FIG. 4, lanes 7–9). IBDV/EK (lane 4) as well as IBDV/VP5⁻ (lane 1) infected CEC showed viral proteins VP2, VP3, and VP4 after precipitation with rabbit anti-IBDV serum. The rabbit anti-VP5 serum (lane 5) and mAb DIE 7 (lane 6) precipitated VP5 with a molecular mass

TABLE 1

Sequence of oligonucleotide primers used for generating mutant constructs.

| ᵃNucleotide sequence | Orientation | Designation | Nucleotide no. |
|---|---|---|---|
| AGAGAATTC*TAATACGACTCACTATA*GGA TACGATCGGTCTGAC | + | A1f5' | 1–18 |
| TGGGCCTGTCACTGCTGTCACATGT | − | A2R | 716–740 |
| CATTGCTCTGCAGTGTGTAGTGAGC | − | A3R | 338–362 |
| CTACAACGCTATCCTTAAGGGTTAGTA GAG | + | VP5MutF | 80–109 |
| CTCTACTAACCCTTAAGGATAGCGTTGT AG | − | VP5MutR | 80–109 | a) Underlined nucleotides denote virus specific nucleotides. T7 promotor sequences are marked in italics. Mutated nucleotides are bold and orientation of the primer is shown for sense (+) and antisense (−). Primer positions are given according to the published sequence of serotype I strain P2 (Mundt et al., Virology 209, 209–218, 1995).

Virus recovery from cRNA. For in vitro transcription of RNA plasmids pAD78/EK, pAD78/VP5⁻ and pBP2 (FIG. 2) were linearized by cleavage with BsrGI and PstI, respectively. Treatment of linearized DNA, transcription and purification of RNA, and transfection were carried out as described by Mundt and Vakharia (1996, supra) with the exception that secondary CEC were used for the transfection experiments. Three days after transfection a CPE was visible in CEC. Cells were freeze/thawed, centrifuged at 700×g to eliminate cellular debris, and the resulting supernatants were of 21 kDa only from IBDV/EK infected cells. No specific reactivity was detectable in IBDV/VP5⁻ infected CEC after precipitation with rabbit-anti VP5 (lane 2) as well as the VP5 specific mAb DIE 7 (lane 3). Non-infected CEC showed no specific reactivity (lanes 7–9).

Figure 5:
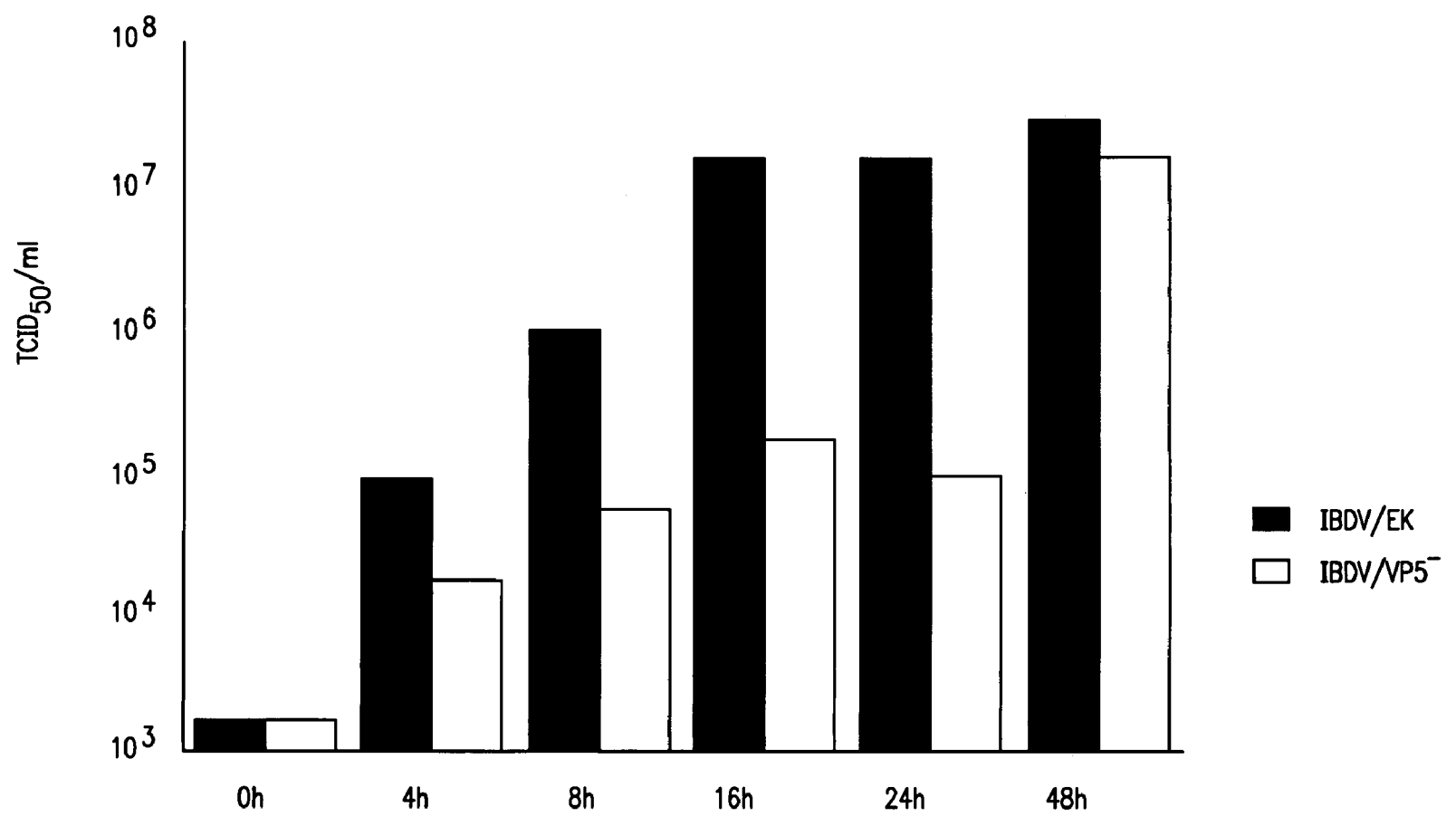

Replication of IBDV/VP5⁻ in CEC. To assay replication of IBDV/VP5⁻ in more detail one step growth was analysed (FIG. 5). Confluent secondary CEC were infected with IBDV/EK and IBDV/VP5⁻ with $10^{7.2}$ TCID$_{50}$, respectively. Immediately after overlaying the infected cells with 5 ml growth medium, supernatant from one infected CEC tissue plate of each virus was removed and stored at −20° C. (0 h p.i.). Remaining tissue culture plates were further incubated and 4h, 8h, 16h, 24h, and 48h p.i. supernatants were removed and stored at −20° C. Supernatants were centrifuged and titrated according to standard methods. The TCID$_{50}$ at the different time points after infection showed that the VP5 expressing virus (IBDV/EK) replicated faster than the virus mutant lacking VP5 (IBDV/VP5$^-$). 16 h after infection IBDV/EK showed a 100-fold higher than IBDV/VP5$^-$ (FIG. 5). However, at 48 h p.i. IBDV/VP5$^-$ reached a titre of 10$^{7.2}$ TCID$_{50}$/ml which was similar to IBDV/EK (10$^{7.45}$/ml).

Preparation of recombinant IBDV VP5$^-$-2. Plasmid pAD78/VP5$^-$-2 was prepared by techniques similar to those described above. The nucleotide sequence of part of the mutated VP5 gene is shown in SEQ ID No. 7 and FIG. 3. A restriction enzyme fragment harbouring the mutations was used to substitute the wild-type EcoRI-NdeI fragment in pAD78/EK. An outline of the protocol for the preparation of the recombinant plasmid is shown in FIG. 3. The organisation of pBD78 is also depicted in FIG. 3. The recombinant virus was prepared as described above, except for the fact that segment B of strain D78 (SEQ ID No. 8) was used and QM-7 cells were used for the transfection experiment.

Example 2

Identification of VP5 Protein in Different IBDV Strains

Different strains of IBDV were investigated for the expression of the VP5-gene. This was done by making use of the immuno-fluorescence technique (IFT). Chicken embryo fibroblasts grown in microtiterplates were infected with different IBDV strains. Three to 5 days after incubation at 37° C. cells were fixed with 70% ethanol, then treated with polyclonal rabbit anti IBDV serum (R1928), polyclonal rabbit anti VP5 serum (RαVP5) or monoclonal antibody directed against VP5 (DIE7), respectively. Binding of the poly- or monoclonal antibodies to the different IBDV strains was visualised by making use of a fluorescence labelled conjugate (goat-anti-rabbit or goat-anti-mouse). The results are shown in Table 2:

TABLE 2

Identification of different sero- and subtypes of IBDV strains. Determination of the presence of VP5 proteins.

| IBDV-serotype | IBDV-subtype | IBDV-strain | R1928 | RαVP5 | DIE7 |
|---|---|---|---|---|---|
| I | Classical | D78 | + | + | + |
| I | Classical | 228TC | + | + | + |
| I | Classical | PBG98 | + | + | + |
| I | Classical | Ram0404 | + | + | + |
| I | Classical | IBDV/EK | + | + | + |
| I | Classical | IBDV/VP5$^-$ | + | − | − |
| I | GLS | GLS | + | + | + |
| I | Variant-E | 8903 | + | + | + |
| II | TY89 | TY89 | + | + | + |

From these data it can be concluded that the different strains of IBDV belonging to different sero- and subtypes do express the VP5-gene. Furthermore, the recombinant VP5$^-$ IBDV vaccine strain can be differentiated from field and vaccine viruses, thereby enabling the recombinant VP5$^-$ virus to be used as a marker vaccine.

Example 3

In Vivo Testing of the Recombinant VP5$^+$ and VP5$^-$ IBDV Vaccines in Comparison with a Commercial Available Live IBDV Vaccine.

Preparation of IBDV vaccine. Primary chicken embryo fibroblast (CEF) cells were prepared at a final concentration of 2×10$^6$/ml. The cells were cultured in Eagles minimum essential medium containing 5% fetal calf serum. To 25 ml of this cell suspension 0.1 ml IBDV/EK or IBDV/VP5$^-$ virus (having an infectious titre of about 3.0 log10 TCID$_{50}$/ml) was added. After incubation for 5 days in a high-humidity incubator at 37° C., the total suspension was used in the animal experiment without further purification. The infectious titre of the supernatant was 10$^{7.1}$ TCID50/ml.

Animal experiment. In this study the potency of different vaccines (VP5 positive strain IBDV/EK and a VP5 negative strain IBDV/VP5$^-$, and the commercial available IBDV vaccine Nobilis strain D78, Intervet International B.V., NL) was investigated. SPF chicks of 3 weeks old were treated as indicated in the treatment schedule.

Treatment Schedule:

| Days after vaccination | Groups | | | |
|---|---|---|---|---|
| | 1 | 2 | 3 | 4 |
| 00 | IBDV/EK | IBDV/VP5$^-$ | D78 | — |
| 03 | x | x1 | x | x |
| 07 | x,b1 | x1,b1 | x,b | x,b1 |
| 14 | x,b1 | x,b1 | x,b1 | x,b1 |
| 20 | x,b1 | x,b1 | x,b1 | x,b1 |
| 21 | ch | ch | ch | ch |
| 24 | x | x | x | x |
| 31 | + | + | + | + |

VP5$^+$ Bursal disease vaccination with VP5 positive vaccine clone, eye-drop route, dose 10$^{4.6}$ TCID$_{50}$/animal, 0.1 ml/animal.

VP5$^-$ Bursal disease vaccination with VP5 negative vaccine clone, eye-drop route, dose 10$^{5.9}$ TCID$_{50}$/animal, 0.1 ml/animal.

D78 Bursal disease vaccination with IBDV VACCINE NOBILIS STRAIN D78, eye-drop route, one field dose.

ch Challenge with Bursal disease virus, Farragher strain F52/70, eye-drop route, dose 10$^{2.0}$ CID$_{50}$/animal, 0.1 ml/animal.

b1 Serological examination; VN-test and/or Western blotting.

x Histological examination (H.E. staining) and MCA-8 ELISA on bursae.

x1 Histological examination (H.E. staining) and MCA-8 ELISA on bursae and reisolation of virus from bursa of Fabricius.

+ Clinical examination and after 10 days histological examination of the bursa.

Detection of Virus in the Bursa of Fabricius.

Three, 7, 14 and 20 days after eye-drop vaccination, animals were sacrificed and blood and bursae obtained. The presence of virus in the bursa was determined with an enzyme-linked immunosorbent assay (ELISA) making use of the monoclonal antibody 8 (MAB-8). MAB-8 is directed specifically against IBDV. Data are depicted in Table 3.

Furthermore, 3 and 7 days after vaccination, bursae from animals of group 2 were investigated for the presence of the recombinant VP5$^-$ virus. For that purpose bursae were homogenised and cultured on chicken embryo fibroblasts. The presence of the VP5$^-$ virus was determined by IFT using polyclonal rabbit sera against IBDV or VP5 or monoclonal antibodies against VP5. From 13 out of 15 bursae (87%) investigated, VP5$^-$ virus could be reisolated and identified (positive for R1928 and negative for RαVP5 and DIE7). This indicates that the virus upon animal passage is still VP5$^-$, indicating that the virus is stable and does not revert to VP5+. Furthermore, by using the different poly- and monoclonal antibodies VP5− vaccine virus can be discriminated from all other vaccine and/or field IBDV viruses. Therefore, the VP5− vaccine may be used as a marker vaccine.

Three days after challenge no virus could be detected in groups 1, 2 and 3 with the MCA-8 ELISA. In contrast, all animals of group 4 (non-vaccinated control group) contained challenge virus in the bursa of Fabricius, 3 days after challenge. The results show that animals vaccinated with recombinant VP5+ (group 1), recombinant VP5− (group 2) and IBDV vaccine Nobilis D78 (group 3) were protected against severe challenge.

TABLE 3

Individual data for detection of virus in the bursa of Fabricius with the MCA-8 ELISA at different days after vaccination or challenge.

| Group↓ | Days after vaccination→ | | | Days after challenge | Protection↓ |
|---|---|---|---|---|---|
| | 3 | 7 | 14 | 20 | 3 |
| | Virus detection by ELISA↓ | | | | |
| 1 VP5+ | 2/8* | 1/7 | 0/2 | 0/3 | 0/5 | 100% |
| 2 VP5− | 0/8 | 0/7 | 0/2 | 0/3 | 0/5 | 100% |
| 3 D78 | 1/8 | 6/7 | 0/2 | 0/3 | 0/5 | 100% |
| 4 — | 0/8 | 0/7 | 0/2 | 0/3 | 5/5 | 0% |

*Number of positive bursae per total number tested.

Detection of Lesions in the Bursa of Fabricius.

The microscopic average lesion score induced by the different IBDV (recombinant) vaccines or the challenge virus are depicted in Table 4.

Before challenge, animals vaccinated with the recombinant VP5+ IBDV vaccine (group 1) or vaccinated with IBDV vaccine Nobilis D78 (group 3) showed mild to moderate lesions in the bursa. Three days after challenge only chronic lesions were observed in the bursa of Fabricius, indicating that the animals of groups 1 and 3 were protected against challenge. Furthermore, 10 days after challenge only very mild lesions (0–20% lymphocytic depletion) were observed in the bursa of the animals vaccinated with VP5+ recombinant IBDV vaccine or with Nobilis vaccine D78. In contrast animals not vaccinated and challenged showed severe lesions 10 days after challenge. In other words all animals (100%) of groups 1 and 3, vaccinated with the VP5+ recombinant IBDV vaccine or with Nobilis vaccine D78 were protected against severe challenge.

Three, 7, 14 and 20 days after vaccination and 3 and 10 days after challenge with the recombinant VP5− IBDV vaccine, animals of group 2 showed no to hardly any lesions (0–20% lymphocytic depletion) in the bursa. All animals of group 2, vaccinated with the VP5− recombinant IBDV vaccine, were protected against severe challenge. When animals vaccinated with the recombinant VP5− IBDV vaccine are compared to animals of groups 1 or 3 (vaccinated with a recombinant VP5+ or commercial available vaccine) the recombinant VP5− vaccine induces less lesions and therefore, is safer, milder than the vaccines tested in this experiment.

Three days post-challenge, all non-vaccinated animals of group 4 showed severe acute lesions in the bursa (total lymphocyte depletion, score 5.0). Ten days after challenge, all animals (17 out of 17 animals) showed total lymphocytic depletion, indicating that these animals were not protected against severe challenge. Animals that died after challenge, all showed severe lesions in the bursa of Fabricius. It was concluded that control group 4 was not protected against severe challenge indicating that the test conditions were optimal.

TABLE 4

Average bursal lesion score at different days after vaccination or challenge. The average lesion score is calculated as follows: all lesion scores from the animals per group on a certain day are added. This number is then divided by the total number of animals investigated in that group on that day. Individual scores range from 1 to 5. Score 0 = no lymphocytic depletion, score 1 = 0–20%; score 2 = 20–40%; score 3 = 40–60%; score 4 = 60–80% and score 5 = 80–100% lymphocytic depletion (total lymphocytic depletion).

| Group↓ | Days after vaccination→ | | | | Days after challenge→ | | Protection↓ |
|---|---|---|---|---|---|---|---|
| | 3 | 7 | 14 | 20 | 3 | 10 | |
| | Bursal lesions score↓ | | | | | | |
| 1 VP5+ | 0.8 | 2.9 | 1.0 | 1.0 | 1.0c | 0.6 | 100% |
| 2 VP5− | 0.0 | 0.0 | 0.5 | 0.0 | 0.0c | 0.1 | 100% |
| 3 D78 | 0.1 | 2.4 | 3.5 | 2.0 | 2.8c | 1.1 | 100% |
| 4 — | 0.0 | 0.0 | 0.0 | 0.0 | 5.0a | 5.0 | 0% | aAcute lesions
cChronic lesions

Serological Response.

The serological response of the animals was determined by measuring the ability of blood serum to neutralise a classical infectious bursal disease virus strain in a virus neutralising (VN) test. Serum was investigated 3, 7, 14 and 20 days after vaccination. The average neutralising titres are shown in Table 5.

The results show that recombinant IBDV vaccine VP5+ applied to chickens of group 1 induced a good and high serological response 20 days after vaccination which is comparable to the serological response of the chickens vaccinated with the commercial IBDV vaccine Nobilis strain D78 (group 3). The recombinant IBDV vaccine VP5− applied to chickens of group 2 induced also a good serological response. A titre of 9.4 log2 was observed 20 days after vaccination. The serological response induced by the recombinant VP5− IBDV vaccine was delayed when compared to the serological response induced by the recombinant IBDV VP5+ vaccine or the commercial IBDV vaccine Nobilis strain D78.

The non-vaccinated group 4 showed no serological response to IBDV.

TABLE 5

Average IBDV-VN-titres for groups 1 to 4 at different days after vaccination, expressed as log2 of the dilution.

| Group | Days after vaccination | | | |
|---|---|---|---|---|
| | 3 | 7 | 14 | 20 |
| 1 VP5+ | ≦1.0 ± 0.0 | 7.1 ± 1.7 | 10.2 ± 1.4 | 11.9 ± 1.8 |
| 2 VP5− | ≦1.0 ± 0.0 | 2.1 ± 1.7 | 6.3 ± 2.9 | 9.4 ± 1.4 |
| 3 D78 | ≦1.0 ± 0.0 | 5.2 ± 2.8 | 10.3 ± 1.3 | 11.6 ± 1.5 |
| 4 — | ≦1.0 ± 0.0 | ≦1.0 ± 0.0 | ≦1.0 ± 0.0 | ≦1.0 ± 0.0 |

Serological Differentiation Between Antisera.

The serological response against VP5 was investigated by making use of western blot analysis. For this purpose the VP5 protein was expressed in the E. coli or baculo expression system. The expressed proteins were separated by SDS PAGE. Next the proteins were electroblotted onto a nitrocellulose membrane. Thereafter, the membrane was cut into lanes and the lanes were incubated with rabbit anti-VP5 serum, chicken serum directed against VP5+ recombinant vaccine, chicken serum directed against VP5− recombinant vaccine or negative serum from SPF chickens. Data are summarised in Table 6. As can be seen from Table 6, the VP5− serum does not induce a serological response against VP5. In contrast the rabbit anti-VP5 serum and chicken serum directed against VP5+ recombinant vaccine do recognise the VP5-protein and thus induces a serological response against VP5. This indicates that chicken serum may be used to investigate if animals are exposed to a virus that expresses the VP5 protein (e.g. field virus) or to the VP5− recombinant vaccine.

TABLE 6

Western blot analysis. Serum from animals vaccinated with VP5+ or VP5− recombinant vaccine as well as SPF chicken serum and anti VP5-rabbit serum were investigated for their reaction with the VP5-protein.

| Identification of serum sample | Immuno-blot |
| --- | --- |
| VP5+ vaccinated animal, serum sample 20d after vaccination | positive |
| VP5− vaccinated animal, serum sample 20d after vaccination | negative |
| Non-vaccinated control, serum sample at 20d | negative |
| Rabbit anti VP5 serum | positive |

Mortality and Clinical Signs.

None of the animals vaccinated with VP5+ IBDV vaccine (group 1), vaccinated with recombinant VP5− IBDV vaccine (group 2) or vaccinated with the commercial IBDV vaccine Nobilis strain D78 (group 3), died or showed clinical signs of infectious bursal disease after challenge, indicating that the animals were protected against severe challenge. All animals in the non-vaccinated control group were not protected against severe challenge.

Example 4

In Vivo Testing of the Recombinant VP5−-2 Vaccine

Preparation of the IBDV vaccines. Primary chicken embryo fibroblasts (CEF) cells were prepared at a final concentration of $2 \times 10^6$/ml. The cells were cultured in Eagles minimum essential medium containing 5% fetal calf serum. To 15 ml of this cell suspension 0.1 ml IBDV/VP5−-2 (D78/D78/VP5−) virus was added. After incubation for 6 days in a high humidity incubator at 37° C., the supernatant was titrated. The infectious titre of the supernatant was $10^{8.2}$ TCID$_{50}$/ml. For the second animal experiment the supernatant was diluted to result in a vaccine dose of $10^{5.5}$ TCID$_{50}$/animal and for the first animal experiment the supernatant was diluted to result in a vaccine dose of $10^{4.0}$ TCID$_{50}$/animal or $10^{5.0}$ TCID$_{50}$/egg.

First animal experiment. The effect of the vaccine is assessed by measurement of the serological response and resistance to challenge obtained from administering a challenge virus at the age of 14 days. The vaccine ($10^{5.0}$ TCID$_{50}$/egg or $10^{4.0}$ TCID$_{50}$/animal of D78/D78/VP5−) was applied in ovo or intramuscularly at day old. Microscopic lesions in the bursa were investigated, 3 and 10 days after challenge. Protection against challenge was determined and the serological response at the age of 14 days old was determined with the VN-test.

1. Average microscopic lesion score in the bursa 3 and 10 days after challenge.

| Days post challenge | Group | | |
| --- | --- | --- | --- |
| | In ovo | Day old | None-vaccinated |
| 3 | 3.3 | 0.0 | 5.0 |
| 10 | 0.2 | 0.0 | 5.0 |

2. Protection after challenge

| | Group | | |
| --- | --- | --- | --- |
| | In ovo | Day old | None-vaccinated |
| % protection | 91.6 | 100 | 0 |

3. Serological response against IBDV

| | Group | | |
| --- | --- | --- | --- |
| | In ovo | Day old | None-vaccinated |
| VN-titre | 6.4 ± 1.7 | 6.4 ± 1.3 | <4.0 ± 0.0 |

VN-titre is expressed as log2 of the dilution. Animals with a titre <4.0 log2 are considered negative Conclusions 1 The D78/D78/VP5− strain is a highly attenuated IBD-virus
2 The virus strain is very mild
3 The virus can induce a serological response
4 The virus can induce protection
5 The virus strain can be applied by intramuscular injection to 1 day old SPF chickens and in ovo to 18-days-old embryonated SPF-eggs Second animal experiment. The effect of the vaccine is assessed by measurement of the serological response against IBDV and resistance to challenge obtained from administering a challenge virus, 21 days after administering the Gumboro vaccine. The vaccine ($10^{5.5}$ TCID$_{50}$/animal of D78/D78/VP5−) was applied via the intramuscular route to 14 days old SPF-chickens. Three, 7, 14, and 20 days after vaccination and 3 days after challenge Bursa, spleen, thymus, liver, duodenum, pancreas, ceacal tonsils and harderian gland were investigated for microscopic lesions. Ten days after challenge Bursae were investigated for microscopic lesions. Sera were tested in the VN-test. And mortality was scored after challenge.

1. Percentage mortality after challenge:

| | Mortality after challenge |
| --- | --- |
| Vaccinated group | 0% |
| Control group | 50% |

2. Microscopic lesions of the vaccinated group before and after challenge:

| Days post Vaccinat. | Bursa | Spleen | Thymus | Liver | Duodeum | Pancreas | Ceacal Tonsils | Harderian Gland |
|---|---|---|---|---|---|---|---|---|
| 3 | 0 | 0 | 0 | 0 | 0 | 0 | 0 | 0 |
| 7 | 0 | 0 | 0 | 0 | 0 | 0 | 0 | 0 |
| 14 | 0 | 0 | 0 | 0 | 0 | 0 | 0 | 0 |
| 20 | 0 | 0 | 0 | 0 | 0 | 0 | 0 | 0 |
| 24 | 0, A | 0 | 0 | 0 | 0 | 0 | 0 | 0 |
| 31 | 0, A | ND | ND | ND | ND | ND | ND | ND |

A = None vaccinated animals showed a lymphocytic depletion score of 5.0 (100%) and 4.25, 3 and 10 days after challenge, respectively. ND = not done.

3. Serological Response after Vaccination:

Conclusions
1. The D78/D78/VP5$^-$ strain is a highly attenuated IBD-virus
2. The virus strain is very mild and does not induce lesions in organs
3. The virus can induce a serological response
4. The virus can induce protection

LEGENDS TO THE FIGURES

FIG. 1 Genomic organization of segment A and segment B of IBDV. The numbers indicate the nucleotide positions of the start, end and coding region on the segments.

FIG. 2 Construction of genomic cDNA clones for the preparation of IBDV/VP5$^-$. Plasmid pAD78/EK contains the complete D78 segment A cDNA encoding the polyprotein (VP2-VP4-VP3) and VP5. Plasmid pBP2 contains the complete strain P2 segment B encoding VP1. Mutations were introduced in plasmid pAD78/VP5$^-$ altering the methionine start codon for VP5 into arginine and creating an artificial Afl II cleavage site. Recombinant plasmids were linearized with the underlined restriction enzymes, followed by T7 polymerase transcription.

FIG. 3 Construction of genomic cDNA clones for the preparation of IBDV/VP5$^-$-2. Plasmid pAD78/EK contains the complete D78 segment A cDNA encoding the polyprotein (VP2-VP4-VP3) and VP5. Plasmid pBD78 contains the complete strain D78 segment B encoding VP1. Mutations were introduced in plasmid pAD78/VP5$^-$ altering the methionine start codon for VP5 into glutamic acid and creating an artificial BstBI cleavage site. Further mutations were introduced in the arginine and glutamine codon. Recombinant plasmids were linearized with the underlined restriction enzymes, followed by T7 polymerase transcription.

FIG. 4 Radioimmunoprecipitation of proteins from CEC infected cells with recombinant IBDV. CEC infected cells with IBDV/VP5$^-$ (lanes 1–3), IBDV/EK (lanes 4–6) and uninfected controls were immunoprecipitated with rabbit anti-IBDV serum (lanes 1, 4, 7), rabbit anti-VP5 serum (lanes 2, 5, 8) and mAb DIE 7 (lanes 3, 6, 9). Position of molecular mass markers (M) is indicated. Location of the viral proteins VP2, VP3, VP4 and VP5 are marked.

FIG. 5 Replication kinetics of IBDV/EK and IBDV/VP5$^-$. Infectious titers of supernatants (vertical axis) are determined at the times indicated.

The invention claimed is:

1. A non-reverting infectious bursal disease virus (IBDV) mutant which is not able to produce a VP5 protein as a result of a mutation in the VP5 gene of the IBDV genome, wherein the mutation comprises the substitution of at least two nucleotides of the start codon of the VP5 gene.

2. The IBDV according to claim 1, wherein the mutant further comprises one or more stop codons in a part of the 5'-end of the VP5 gene that does not overlap with the large open reading frame (ORF).

3. The IBDV mutant according to claim 2, wherein the mutant comprises a stop codon in each of the three ORFs.

4. The IBDV mutant according to claim 1, wherein the mutation is in the genome of a virulent field virus.

5. The IBDV mutant according to claim 1, wherein the mutation is in the genome of a vaccine strain.

6. The IBDV mutant according to claim 5, wherein the vaccine strain is strain D78.

7. The IBDV mutant according to claim 1, which expresses a chimeric VP2 protein comprising neutralizing epitopes of different antigenic IBDV types.

8. A vaccine against an IBDV infection in animals, comprising an IBDV mutant according to any one of claims 1–7, and a pharmaceutically acceptable carrier.

* * * * *

SEQUENCE LISTING

<160> NUMBER OF SEQ ID NOS: 14

<210> SEQ ID NO 1
<211> LENGTH: 17
<212> TYPE: PRT
<213> ORGANISM: Artificial Sequence
<220> FEATURE:
<223> OTHER INFORMATION: Synthesized peptide derived from third hyper V
      region of IE molecule Mus musculus

<400> SEQUENCE: 1

Ala Ser Phe Glu Ala Gln Gly Ala Leu Ala Asn Ile Ala Val Asp Lys
 1               5                  10                  15

Ala

```
<210> SEQ ID NO 2
<211> LENGTH: 15
<212> TYPE: PRT
<213> ORGANISM: Artificial Sequence
<220> FEATURE:
<223> OTHER INFORMATION: Synthesized peptide derived from the bole I
      protein of Epstein Barr virus

<400> SEQUENCE: 2

Thr Arg Asp Asp Ala Glu Tyr Leu Leu Gly Arg Glu Ser Val Leu
 1               5                  10                  15

<210> SEQ ID NO 3
<211> LENGTH: 16
<212> TYPE: PRT
<213> ORGANISM: Artificial Sequence
<220> FEATURE:
<223> OTHER INFORMATION: Synthesized peptide derived from the hemophilus
      influenza virus

<400> SEQUENCE: 3

Thr Ser Phe Pro Met Arg Gly Asp Leu Ala Lys Arg Glu Pro Asp Lys
 1               5                  10                  15

<210> SEQ ID NO 4
<211> LENGTH: 36
<212> TYPE: PRT
<213> ORGANISM: Artificial Sequence
<220> FEATURE:
<223> OTHER INFORMATION: Synthesized peptide derived from the TCR
      receptor gene of Mus musculus

<400> SEQUENCE: 4

Leu His Ile Ser Ala Val Asp Pro Glu Asp Ser Ala Val Tyr Phe Cys
 1               5                  10                  15

Ala Ser Ser Gln Glu Phe Phe Ser Ser Tyr Glu Gln Tyr Phe Gly Pro
            20                  25                  30

Gly Thr Arg Leu
        35

<210> SEQ ID NO 5
<211> LENGTH: 9
<212> TYPE: PRT
<213> ORGANISM: Artificial Sequence
<220> FEATURE:
<223> OTHER INFORMATION: Synthesized peptide derived from the influenza
      virus

<400> SEQUENCE: 5

Gly Ile Leu Gly Phe Val Phe Thr Leu
 1               5

<210> SEQ ID NO 6
<211> LENGTH: 9
<212> TYPE: PRT
<213> ORGANISM: Artificial Sequence
<220> FEATURE:
<223> OTHER INFORMATION: Synthesized peptide derived from the influenza
      virus

<400> SEQUENCE: 6

Val Lys Leu Gly Glu Phe Tyr Asn Gln
 1               5

<210> SEQ ID NO 7
<211> LENGTH: 11
```

```
<212> TYPE: PRT
<213> ORGANISM: Artificial Sequence
<220> FEATURE:
<223> OTHER INFORMATION: Synthesized peptide totally artificial
<220> FEATURE:
<223> OTHER INFORMATION: Xaa in position 2 stands for cyclohexylalanine.

<400> SEQUENCE: 7

Lys Xaa Val Ala Ala Trp Thr Leu Lys Ala Ala
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: Synthesized peptide derived from the influenza
      virus

<400> SEQUENCE: 8

Pro Lys Tyr Val Lys Gln Asn Thr Leu Lys Leu Ala Thr
 1               5                  10

<210> SEQ ID NO 9
<211> LENGTH: 17
<212> TYPE: PRT
<213> ORGANISM: Artificial Sequence
<220> FEATURE:
<223> OTHER INFORMATION: Synthesized peptide derived from the ovalbumin
      of Mus musculus

<400> SEQUENCE: 9

Ile Ser Gln Ala Val His Ala Ala His Ala Glu Ile Asn Glu Ala Gly
 1               5                  10                  15

Arg

<210> SEQ ID NO 10
<211> LENGTH: 15
<212> TYPE: PRT
<213> ORGANISM: E. coli
<220> FEATURE:
<223> OTHER INFORMATION: dnaJp1 heat shock protein

<400> SEQUENCE: 10

Gln Lys Arg Ala Ala Tyr Asp Gln Tyr Gly His Ala Ala Phe Glu
 1               5                  10                  15

<210> SEQ ID NO 11
<211> LENGTH: 15
<212> TYPE: PRT
<213> ORGANISM: Homo sapiens

<400> SEQUENCE: 11

Gln Lys Arg Ala Ala Val Asp Thr Tyr Cys Arg His Asn Tyr Gly
 1               5                  10                  15

<210> SEQ ID NO 12
<211> LENGTH: 9
<212> TYPE: PRT
<213> ORGANISM: Homo sapiens

<400> SEQUENCE: 12

Gly Ile Leu Gly Phe Val Phe Thr Leu
 1               5

<210> SEQ ID NO 13
```

-continued

```
<211> LENGTH: 9
<212> TYPE: PRT
<213> ORGANISM: Homo sapiens

<400> SEQUENCE: 13

Val Lys Leu Gly Glu Phe Tyr Asn Gln
 1               5

<210> SEQ ID NO 14
<211> LENGTH: 13
<212> TYPE: PRT
<213> ORGANISM: Homo sapiens

<400> SEQUENCE: 14

Pro Lys Tyr Val Lys Gln Asn Thr Leu Lys Leu Ala Thr
 1               5                  10
```